United States Patent [19]

Meinert et al.

[11] Patent Number: 5,441,989
[45] Date of Patent: Aug. 15, 1995

[54] VITREOUS HUMOR TAMPONADE FOR THE POSTERIOR CAVITY IN AN EYE

[75] Inventors: Hasso Meinert, Neu-Ulm; Klaus Heimann, Köln; Christine F. Kreiner, München; Bernd Kirchhof, Köln, all of Germany

[73] Assignee: adatomed Pharmazeutische und medizintechnische Gesellschaft mbh, Munich, Germany

[21] Appl. No.: 81,050

[22] Filed: Jun. 25, 1993

[30] Foreign Application Priority Data

Jun. 25, 1992 [DE] Germany .................. 42 20 882.3

[51] Int. Cl.⁶ .............................................. A61K 31/08
[52] U.S. Cl. ...................................... 514/772; 514/912
[58] Field of Search ........................ 514/772, 832, 912

[56] References Cited

U.S. PATENT DOCUMENTS

| 4,490,351 | 12/1984 | Clark et al. | 424/5 |
| 5,037,384 | 8/1991 | Chang | 604/28 |

FOREIGN PATENT DOCUMENTS

| 493677 | 11/1991 | European Pat. Off. |
| 8303201 | 9/1983 | WIPO |
| 9216240 | 10/1992 | WIPO |

OTHER PUBLICATIONS

Constable, Investigative Ophthalmology, "A Journal of Clinical and Basic Research," Aug. 1974, vol. 13/8, pp. 627–629.

Chang et al., Perfluorocarbon Gases in Vitreous Surgery, "Ophthalmology," vol. 92, No. 5, May 1985, pp. 651–656.

Claes et al., "The Use of Perfluorocarbon Liquids in Vitreous Surgery," Bull. Soc. Belge Ophthalmology, vol. 238, 1990.

*Primary Examiner*—Zohreh Fay
*Attorney, Agent, or Firm*—Keck, Mahin & Cate

[57] ABSTRACT

A vitreous humor tamponade for the posterior cavity in an eye, including at least one perfluorocarbon which is liquid under normal conditions and which after injection in the eye changes into the vapor condition as a result of its vapor pressure.

1 Claim, No Drawings

VITREOUS HUMOR TAMPONADE FOR THE POSTERIOR CAVITY IN AN EYE

BACKGROUND OF THE INVENTION

The present invention concerns a vitreous humor tamponade for the posterior cavity in an eye such as a human eye, in particular for the treatment of retinal detachment.

Relevant state of the art is described in the following literature:

Aronowitz JD and Brubaker RF; Effect of intraocular gas on intraocular pressure; Arch Ophthalmol, 94 (1976) 1191-6;

Cibis PA, Becker B, Okun E and Canaan S; The use of liquid silicone in retinal detachment; Arch Ophthalmol, 68 (1962) 590-9;

Custodis E; Die Behandlung der Netzhautablösung durch umschriebene Diathermiekoagulation und einer mittels Plcmbenaufnäihung erzeugten Eindellung der Sklera im Bereich des Risses; Klin Monatsbl Augenheilkd, 129 (1956) 476-95;

Dimopoulos S and Heimann K; Spätkomplikationen nach Silikonölinjektion. Langzeitbeobachtung an 100 Fällen; Klin Monatsbl Augenheilkd, 189(1986) 223-7;

Freeman WU, Lipson BK, Morgan CM and Liggett PE; New posteriorly located retinal breaks after pneumatic retinopexy; Ophthalmology, 95 (1988) 14-8;

Kanski JJ, Elkington AR and Daavies MS; Diplopia after retinal detachment surgery; AM J Ophthalmol, 76 (1973) 38-40;

Lemmen KD, Dimopoulos S, Kirchhof B and Heimann K; Keratopathy following pars plana vitrectomy with silicone oil filling; Dev Ophthalmol, 13 (1987) 88-98;

Lucke K and Laqua H; Silicone oil in the treatment of complicated retinal detachment; Springer, Berlin, Heidelberg, NY, 1990, 61-6;

Lund OE and Pesch KJ; Über Früh- und Spätfolgen nach bulbusumschnürenden Operationen; Ber Dtsch Ophthal Ges, 67 (1965) 202-12;

Machemer R, Buettner H, Norton EWD and Parel JM; Vitrectomy. A pars plana approach; Trans Am Acad Ophthalmol Otolaryngol 75 (1971) 813-20;

Norton EDW; Intraocular gas in the management of selected retinal detachments; Trans Am Ophthalmol Otolaryngol, 77 (1973) 85-98;

Rubin ML; The induction refractive errors by retinal detachment surgery; Trans Am Ophthalmol Soc 73 (1975) 452-90;

Russo CE and Ruiz RS; Silicone sponge rejection. Early and late complications in retinal detachment surgery; Arch Ophthalmol, 85 (1971) 647-50; and Stinson TW and Donlon JY; Interaction of intraocular air and sulfur hexafluoride with nitron oxide: a computer simulation; Anesthesiology, 56 (1982) 385-8.

Therefore essentially the following procedures are known for the treatment of retinal detachment:

lead seal means or strips are sewn on to the eye. In that way the traction effect which the vitreous humor causes in the region of the hole in the retina is relieved and the foramen itself is tamponned from the outside; and gases such as $SF_6$, $CF_4$, $C_2F_6$, $C_3F_8$ and inert gases such as krypton or xenon, which are referred to as gas tamponades, or liquids, for example silicone oil, referred to as liquid tamponades, are injected into the vitreous cavity, thereby providing an internal tamponade effect for the hole in the retina.

Those procedures for retinal tamponade involve a number of difficulties which can also be found in the above-indicated literature:

a) The indentation operations are extensive. Large wound areas occur as the conjunctiva has to be opened up and a lead sealing or cerlage bed has to be prepared. The operation requires retrobulbar pain control or intubation narcosis and takes between about 50 and 60 minutes and requires the patient to stay in hospital in a stationary condition for about a week.

In that respect there is the risk of restriction of postoperative eye mobility with consequential double vision (Kanski et al, 1973).

In addition a vision defect such as for example myopia may be induced and increased ( Rubin, 1975).

Circulation of blood to the chorioid is impeded and in addition the chorioid is the point of origin of bleeding into the interior of the eye (Lund, 1965).

The seal or strip material can be rejected, it can suffer from infection and then pierce its way to the outside through the conjunctiva (Russo et al, 1971).

b) The primary gas tamponade is inevitably incomplete as, having regard to the pressure of the eye, only a maximum of one-eighth of the volume of the posterior cavity is tamponned. The patient is required constantly to maintain a head attitude which is often uncomfortable, so that the gas bubble is moved to a position in front of the hole in the retina. For reasons which are unknown at the present time the gas bubble expands to a maximum of double the injected volume (Aronowitz, 1976, Stinsen et al, 1982).

The high degree of mobility of the incomplete tamponade relative to the rest of the vitreous humor, of gel nature, induces vitreo-retinal stresses which in between 10 and 24% of cases induce secondary retinal holes mostly in the lower circumference (Freeman et al, 1988).

c) Tamponade using silicone oil presupposes that firstly the vitreous humor is removed by surgical operation (vitrectomy).

The silicone oil impedes lens nourishment so that a cataract is formed (Dimopoulos et al, 1986).

The silicone oil emulsifies and causes secondary glaucoma (Lucke et al, 1990). A second operation is required to remove silicone oil from the eye again. The silicone oil, when contact occurs, induces irreversible clouding of the cornea (strip degeneration, Lemmen et al, 1987).

SUMMARY OF THE INVENTION

An object of the present invention is to provide a more suitable and as complete a vitreous humor substitute as possible which can be injected without previous suction removal of the vitreous humor.

Another object of the present invention is to provide a vitreous humor tamponade for the posterior cavity in a human eye, which affords a high level of effectiveness but without involving operative complications such as gas injection or previous vitrectomy.

In accordance with the principles of the present invention the foregoing and other objects are achieved by a vitreous humor tamponade for the posterior cavity in a human eye, including at least one perfluorocarbon. The perfluorocarbon is liquid under normal conditions and goes into the vapor condition after injection in the eye as a result of its inherent vapor pressure.

DETAILED DESCRIPTION

The invention thus provides a vitreous humor tamponade for a treatment procedure, in particular for dealing with retinal detachment caused by a hole. That procedure can be employed to replace the following:

a) the indentation operation (operation of Custodis, 1956);

b) direct gas tamponade (Norton, 1973);

c) silicone oil tamponade (Cibis, 1962).

The vitreous humor tamponade according to the present invention means that there is no need for the vitreous humor to be removed by suction beforehand (vitrectomy in accordance with Machemer, 1971).

It is thus possible to provide for a complete tamponade effect for the posterior cavity without initial suction removal of the vitreous humor and without the injection of a gas. The perfluorocarbon (which can be referred to in abbreviated form as PFC) is injected into the eye, in liquid form, at ambient temperature. The injection volume in the case of a human being may be only about 8 $\mu$l, so that with a total volume for the vitreous humor of 4000 $\mu$l, the injection volume fills only about 0.2% of that volume. In the posterior cavity the PFC-liquid (which can be referred to in abbreviated form as PFCL) is heated to body temperature of about 37° C. and gradually changes into the gaseous phase. Because of its vapor pressure therefore the PFCL, on changing into the gaseous phase, gradually assumes a volume which is about 500 times greater than the liquid volume of the primarily injected perfluorocarbon liquid. The perfluorocarbon which is injected in that way may remain in the posterior cavity in the form of a gas bubble for weeks and is gradually resorbed by way of the vascularised eye integuments or chorioid.

The vitreous humor cavity is completely filled, with displacement of the water component. The injection location is the pars plana of the ciliary body. Gradual evaporation of the PFCL permits the water to be dispelled from the posterior cavity (99% proportion of water) without the intraocular pressure rising to an unacceptably high level.

Finally the tamponade fills up the whole of the posterior cavity. Therefore, unlike the situation when using the primary vitreous humor injection method, those retina holes which are located in the lower periphery are also tamponned. That constitutes a corresponding enlargement in terms of indication of the vitreous humor tamponade.

After a period of five weeks the perfluorocarbon used for vitreous humor tamponade purposes has been spontaneously resorbed.

It is known that pure perfluorocarbons are chemically and physiologically extremely inert compounds (see H. Meinert European patent No (European patent application No 91 120184.6)). Perfluorocarbons have very low surface tensions (<30 dyn/cm) and relatively high density values (1.5–1.9 g/cm$^3$) and high vapor pressures. PFCLs are not soluble in water. Boiling point and melting point rise with increasing molecular weight while conversely the vapor pressure falls.

PFCLs have high levels of solubility for gases, inter alia for nitrogen, air, inert gases $O_2$, $CO_2$ and $SF_6$. The PFCLs which are of interest from the point of view of ophthalmology are colorless liquids which are also highly suitable in terms of a laser treatment because they do not suffer from any decomposition in that situation. The gas solubility thereof is in accordance with Henry's law, that is to say, at a constant temperature, solubility is proportional to the partial pressure of the gas. In addition solubility depends on the molecular weight of the gas to be dissolved. The higher the molecular weight the higher is the level of solubility in the PFCL. Under normal conditions the solubility of $O_2$ is 40–50% by volume, that of $CO_2$ is 100–150% by volume and that of $SF_6$ is 600–900% by volume (with a low degree of dependency on the respective PFCL used). However, even gaseous perfluorocarbons such as $CF_4$, $C_2F_6$, $C_3F_8$ and cyclic $C_4F_8$ are highly soluble in liquid perfluorocarbons (PFCLs). Depending on the prevailing physical conditions (pressure and temperature), the constitution of the gas and the amount of the gas to be dissolved, there is a further variation in the vapor pressure of the mixture.

Therefore the overall vapor pressure of the system can be varied in a desirable range in dependence on the inherent vapor pressure of the PFCL to be used, its high solubility for gases in accordance with Henry's law and the molecular weight of the gas to be dissolved.

The vapor pressure which obtains after injection of the PFCL into the eye can also be achieved solely in consideration of the nature of the PFCL used. In that respect, compounds with boiling points of between 40° C. and 70° C. are preferably recommended as the PFCLs. Such compounds include more especially perfluorocarbons such as perfluoro-n-pentane, perfluoro-n-hexane, perfluoro-n-heptane and perfluoromethyl-cylopentane.

The advantage of the above-indicated PFCLs is that they can still be handled in the form of liquids under the conditions obtaining in the operating theater and accordingly can also be injected in accurately metered amounts.

In that connection, as already stated, the PFCLs to be used can also be varied in regard to the desired vapor pressures by way of saturation with the above-mentioned gases, with their vapor pressures. In that respect it is desirable for saturation to be effected with gases at ambient temperature or 37° C.

The PFCL or a PFCL saturated with one or more of the above-mentioned gases is injected into the eye at ambient temperature (25° C.), as described above. In the case of a human being, the injection volume is about 8 $\mu$l and therefore, with a total volume for the vitreous humor of about 4000 $\mu$l, the injection volume fills up only about 0.2% of the volume of the posterior cavity. In the posterior cavity the PFCL is heated to body temperature of about 37° C. and gradually changes into a gaseous phase, in which respect an intraocular pressure of 30 mm Hg is not to be exceeded a long term. The PFCL injected in that way remains in the posterior cavity in the form of a gas bubble for a period of weeks, for example three weeks, and is progressively resorbed by way of the vascularised eye integuments. With the above-mentioned PFCLs or gas-saturated PFCLs, the tamponade spontaneously resorbed after about five weeks.

It will be appreciated that the above detailed description of the invention only sets out the invention by way of example and illustration thereof and that various alterations and modifications may be made therein without thereby departing from the spirit and scope of the invention.

What is claimed is:

1. A method of using a perfluorocarbon, which is liquid under normal conditions and which after injection into an eye gradually changes to vapor condition as a result of its inherent vapor pressure at body temperature, as a displacement agent for eliminating a water component from a posterior cavity in a non-vitrectomised eye, comprising:
  a) injecting a liquid perfluorocarbon into a posterior cavity of a non-vitrectomised eye;
  b) gradually forming a gas bubble of the injected liquid perfluorocarbon, as a result of its inherent vapor pressure at body temperature;
  c) displacing and thereby eliminating a water component from the posterior cavity in the non-vitrectomised eye by replacing the water component with the gas bubble.

* * * * *